US009687712B2

(12) United States Patent
Statham et al.

(10) Patent No.: US 9,687,712 B2
(45) Date of Patent: Jun. 27, 2017

(54) METHOD AND SYSTEM FOR FEEDBACK ON RUNNING STYLE FIELD AND BACKGROUND OF THE INVENTION

(75) Inventors: Andrew Statham, Delft (NL); Marcus Benedictus Hoppenbrouwers, Delft (NL)

(73) Assignee: Nederlandse Organisatie voor toegepast-naturrweten schappelijk onderzoek TNO, Delft (NL)

( * ) Notice: Subject to any disclaimer, the term of this patent is extended or adjusted under 35 U.S.C. 154(b) by 352 days.

(21) Appl. No.: 14/235,920

(22) PCT Filed: Aug. 9, 2012

(86) PCT No.: PCT/NL2012/050553
§ 371 (c)(1),
(2), (4) Date: Mar. 21, 2014

(87) PCT Pub. No.: WO2013/022344
PCT Pub. Date: Feb. 14, 2013

(65) Prior Publication Data
US 2014/0195023 A1    Jul. 10, 2014

(30) Foreign Application Priority Data
Aug. 9, 2011    (EP) .................................. 11176967

(51) Int. Cl.
*A63B 69/00*    (2006.01)
*A61B 5/103*    (2006.01)

(52) U.S. Cl.
CPC ........ *A63B 69/0028* (2013.01); *A61B 5/1038* (2013.01)

(58) Field of Classification Search
CPC .... A61B 5/1038; A61B 5/6807; A61B 5/7225
See application file for complete search history.

(56) References Cited

U.S. PATENT DOCUMENTS

| 4,578,769 A | 3/1986 | Frederick |
| 4,763,287 A | 8/1988 | Gerhaeuser et al. |

(Continued)

FOREIGN PATENT DOCUMENTS

| EP | 2422698 A1 | 2/2012 |
| JP | 6340577 | 2/1988 |

(Continued)

OTHER PUBLICATIONS

Hasegawa et al, "Foot Strike Patterns of Runners at the 15KM Point During an Elite-Level Half Marathon", Journal of Strength & Conditioning Research, Aug. 2007.

(Continued)

*Primary Examiner* — Reginald Renwick
(74) *Attorney, Agent, or Firm* — Hoffmann & Baron, LLP

(57) ABSTRACT

The invention relates to a system and method for providing feedback to a user on his or her running style or running technique. The system employs a pressure sensitive surface to record a gait line of the center of pressure exerted by the user's foot on an underlying surface during a footstep period. In case of a fore or mid-foot landing the gait line may be observed to move backwards with respect to the sagittal plane. From a backwards-going gait line two time stamps are determined. The first timestamp T1 is the time that the foot strikes the ground. The second timestamp T2 is the time that the gait line reaches the most backward position. From the time difference between these two timestamps a loading time dT is determined. The reactivity of the running style describes the viscoelastic behavior of the muscle-tendon unit and may be calculated as a function of this loading time and/or the distance moved by the center of pressure backwards towards the heel. Correspondingly, a feedback signal may be provided to the user about his running reactivity.

15 Claims, 7 Drawing Sheets

(56) References Cited

U.S. PATENT DOCUMENTS

| | | | |
|---|---|---|---|
| 5,921,004 | A | 7/1999 | Lyden |
| 6,360,597 | B1 | 3/2002 | Hubbard, Jr. |
| 7,921,716 | B2 * | 4/2011 | Morris Bamberg . A43B 3/0005 73/379.05 |
| 2002/0040601 | A1 | 4/2002 | Fyfe et al. |
| 2005/0131317 | A1 | 6/2005 | Oddsson et al. |
| 2007/0275830 | A1 | 11/2007 | Lee et al. |
| 2011/0146396 | A1 | 6/2011 | Kim et al. |
| 2011/0208444 | A1 * | 8/2011 | Solinsky ............... A61B 5/112 702/41 |
| 2012/0035509 | A1 * | 2/2012 | Wilson ............... A61B 5/1038 600/592 |

FOREIGN PATENT DOCUMENTS

| | | |
|---|---|---|
| JP | 2004201885 | 7/2004 |
| JP | 2009106391 | 5/2009 |
| SU | 1326269 A1 | 7/1987 |
| TW | 551195 | 9/2003 |
| TW | 200821015 A | 5/2008 |
| TW | I307635 B2 | 3/2009 |
| WO | 9944016 | 9/1999 |
| WO | 2008030091 A1 | 3/2008 |
| WO | 2008039082 A2 | 4/2008 |
| WO | WO2009124193 | 10/2009 |
| WO | 2011002788 A2 | 1/2011 |

OTHER PUBLICATIONS

Fredericson, et al, "Hip Abductor Weakness in Distance Runners with Iliotibial Band Syndrome", Clinical Journal of Sport Medicine, vol. 10, pp. 169-175, 2000.

Couillandre, et al, "How does the heel-off posture modify gait initiation parameter programming", J Mot Behav. Sept 35(3):221-7, 2003.

Hennig, et al, "In-Shoe Pressure Distribution for Running in Various Types of Footwear", Journal of Applied Biomechanics, vol. 11, pp. 299-310, 1995.

Arendse, et al, "Reduced Eccentric Loading of the Knee with the Pose Running Method, Medicine & Science in Sports & Exercise", vol. 36, Issue 2, pp. 272-277, Feb. 2004.

Cavagna, et al, "The Mechanics of Sprint Running", J. Physiol, vol. 217, pp. 709-721, 1971.

R. Herren, et al, "The prediction of speed and incline in outdoor running in humans using accelerometry", Med Sci Sports Exerc, 31(7) 1053-9, Jul. 1999.

Kristine Nielsen, "The Relationship between Plantar Loading and Rearfoot Motion during Walking", Faculty Sponsor: Thomas W. Kernozek, Ph.D., Physical Therapy Department.

Taylor, et al, "Viscoelastic properties of muscle-tendon units", The American Journal of Sports Medicine, vol. 18, No. 3, 1990.

* cited by examiner

METHOD AND SYSTEM FOR FEEDBACK ON RUNNING STYLE FIELD AND BACKGROUND OF THE INVENTION

FIELD AND BACKGROUND OF THE INVENTION

The present invention relates to a system and method for analysis and feedback of a subject's running style or running technique, in particular to a system and method that automatically provides feedback on a subject's running reactivity.

In the field of running, different theories exist as to the optimal style that should be used for running faster, longer, and/or minimize the risk of injuries. In particular different types of running methods are advocated by different parts of the running community. On the one hand there is the so-called "Pose method" of running developed by Nicholas Romanov. One philosophy behind the Pose running style is that the runner should avoid up- and downward movements as much as possible while running, since this would expend unnecessary energy. On the other hand there is the so-called Bosch and Klomp style of running, also referred to as the "BK method", developed by Frans Bosch and Ronald Klomp. One philosophy behind the BK method is that a runner can recover part of his expended energy during running by using the elasticity of his body and in particular the muscles and tendons in his leg and foot section. In the BK method, the runner is thus encouraged to "bounce" up and down while running, which is in stark contrast to the Pose method. Further reference material and specifics on these methods can be found e.g. in the books *"Dr. Romanov's Pose method for running"* and *"Running: Biomechanics and Exercise Physiology in Practice"* (2005) by Frans Bosch and Ronald Klomp.

Efficiency in running refers to the ratio of the amount of (desired) work done by the athlete to the amount of energy used. To achieve better efficiency it is advantageous to reduce the amount of "wasted" energy and/or to try to recover and reuse part of the expended energy.

"Reactive running" is a term used in running and in particular by the Bosch and Klomp running school. Reactivity refers to the amount of energy that is reused for the purpose of performing useful work, in this case running. Running more reactively means that more expended energy is reused from one step to the next, and running less reactive means that less or no energy is reused and thus is absorbed or cushioned by damping structures in the body.

The "running reactivity" is a measure of how reactive or spring-like/elastic the steps of a user are during a running activity (as opposed to viscous). In terms of running reactivity, the Pose method and BK method are on two extreme points of a scale, wherein the Pose method strives for minimal impact, essentially reducing reactivity (no bounce) utilizing the more viscous behavior of the muscle-tendon unit to reduce impact while the BK method strives for high reactivity (maximum bounce or spring action) utilizing the more elastic behavior of the muscle-tendon unit to return more energy. For a runner it can be advantageous to know on which part of the scale his running style is located. By receiving feedback on his reactivity, the runner can choose and/or adjust his movement e.g. to emphasize or avoid one or the other type of running style, the less reactive style with more viscous behavior of the muscle tendon unit will result in more energy being absorbed, thus lowering impact experienced by the runner, the more reactive style with more elastic behavior will result in more energy being returned to the runner, but the runner may experience higher impact.

Taylor et al. (Am. J. Sports Med June 1990 vol. 18 no. 3 300-309) describe the viscoelastic behavior of the muscle-tendon unit. As with most biological tissues, muscle is thought to act viscoelastically. Therefore, muscle is considered to have both elastic and viscous properties. Elasticity implies that length changes, or deformations, are directly proportional to the applied forces, or loads. Viscous properties are characterized as time-dependent and rate change-dependent, where the rate of deformation is directly proportional to the applied forces. In biomechanics, true elasticity is represented by Hooke's model of a perfect spring and viscous elements are represented by Newton's model of a hydraulic piston, known as a dashpot. Biomechanical models attempt to represent viscoelastic behavior by combining springs and dashpots in various configurations.

A person's running style can in principle be evaluated by a trained observer, e.g. a personal coach, familiar with various running techniques. It is however desirable to more objectively quantify a running style, in particular to measure or determine a running reactivity as a quantifiable property. Systems for automatically deriving some aspects of a subject's movement pattern during a running activity are known in the art. For example, US patent application 2002/0040601 discloses a motion analysis system comprising accelerometers and a tilt sensor that are mounted on a shoe. This known system measures gait parameters to determine a running velocity and distance traveled. A disadvantage of using accelerometers for deriving movement patterns is that the method can become less accurate if the accelerometers are mounted incorrectly and/or if they become disorientated during use, thus requiring constant calibration. Accelerometers are also very vulnerable for disturbances from vibrations, and unstable, incorrect or loose mounting. Accelerometers are limited to measuring the dynamic elements of the body they are in direct contact with (i.e. the shoe or foot of a runner), the more static phases of movement (stance phase in running) cannot be so easily measured utilizing accelerometry.

There is a need for a practical measurement technique for analyzing foot dynamics in particular of its viscoelastic behavior for assessing the running efficiency, risk of injury or comfort of a user. There is a further need for a method that provides objective feedback on a subject's running reactivity, the method using a simple analysis of data provided by straightforward sensor measurements of the subject's movements. There is also a need for a system for providing and analyzing said data, a system that is straightforward to implement, e.g. using simple sensors and equipment, and also provides a comfort and ease of use for the running subject.

SUMMARY OF THE INVENTION

In a first aspect there is provided a system for generating feedback on a subject's running style or running technique. The system comprises a pressure sensitive surface, a clock, a memory, a read out device, a processor, and a feedback device. The pressure sensitive surface comprises a plurality of pressure sensors for generating an electronic signal as a function of a pressure exerted on said pressure sensitive surface. The clock is arranged for providing timestamp information. The memory is arranged for storage and retrieval of data. The readout device is arranged for reading out the plurality of pressure sensors and the clock and storing data in the memory comprising a time-dependent measurement of a moving center of pressure exerted by the subject's foot on the pressure sensitive surface. The moving center of pressure forms a pressure gait line that is at least distinguished along a forward axis of a running direction. The feedback device arranged for generating one or more of a visual, audio, or haptic feedback signal and controlled by a processor. The processor is arranged for reading the data from the memory, determining from the data a first timestamp at a first registered moment that the subject's foot starts touching the ground, determining from the data a second timestamp at a moment that the center of pressure reaches the most backwards registered position along the gait line with respect to the forward axis, calculating a time difference between the first and second timestamps as a defined loading time, and controlling the feedback device to generate a feedback signal as a function of the loading time.

In a second aspect there is provided a method for generating feedback on a subject's running style. The method comprises the step of receiving data comprising a time-dependent measurement of a moving center of pressure exerted by the subject's foot on a pressure sensitive surface. The moving center of pressure forms a pressure gait line that is at least distinguished along a forward axis of a running direction. The method further comprises the steps of determining from the data a first timestamp at a first registered moment that the subject's foot starts touching the ground, determining from the data a second timestamp at a moment that the center of pressure reaches the most backwards registered position along the gait line with respect to the forward axis, calculating a time difference between the first and second timestamps as a defined loading time, and controlling the feedback device to generate a feedback signal as a function of the loading time.

In a third aspect there is provided a human interface device wearable on a subject's wrist or arm for providing a user with feedback on a running style. The device comprises a wireless transceiver, a display, and attachment means. The wireless transceiver is arranged for receiving a signal indicative of the subject's running style. Running reactivity is defined in this case as a parameter inversely proportional to a measured time period between a first moment that a foot of the subject hits the ground and a second moment that a center of pressure, exerted by the subject's foot reaches a most backward position with respect to the subject's running direction. The display is arranged for displaying an image as a function of the received signal of the subject's running reactivity. The attachment means are arranged for attaching the display to the subject's wrist or arm Further advantages and areas of applicability of the present systems and methods will become apparent from the detailed description provided hereinafter. It should be understood that the detailed description and specific examples, while indicating exemplary embodiments of the method and system for automatic posture evaluation, are intended for purposes of illustration only and are not intended to limit the scope of the invention.

BRIEF DESCRIPTION OF THE DRAWINGS

These and other features, aspects, and advantages of the apparatus, systems and methods of the present invention will become better understood from the following description, appended claims, and accompanying drawing wherein:

DETAILED DESCRIPTION

Figure 1:
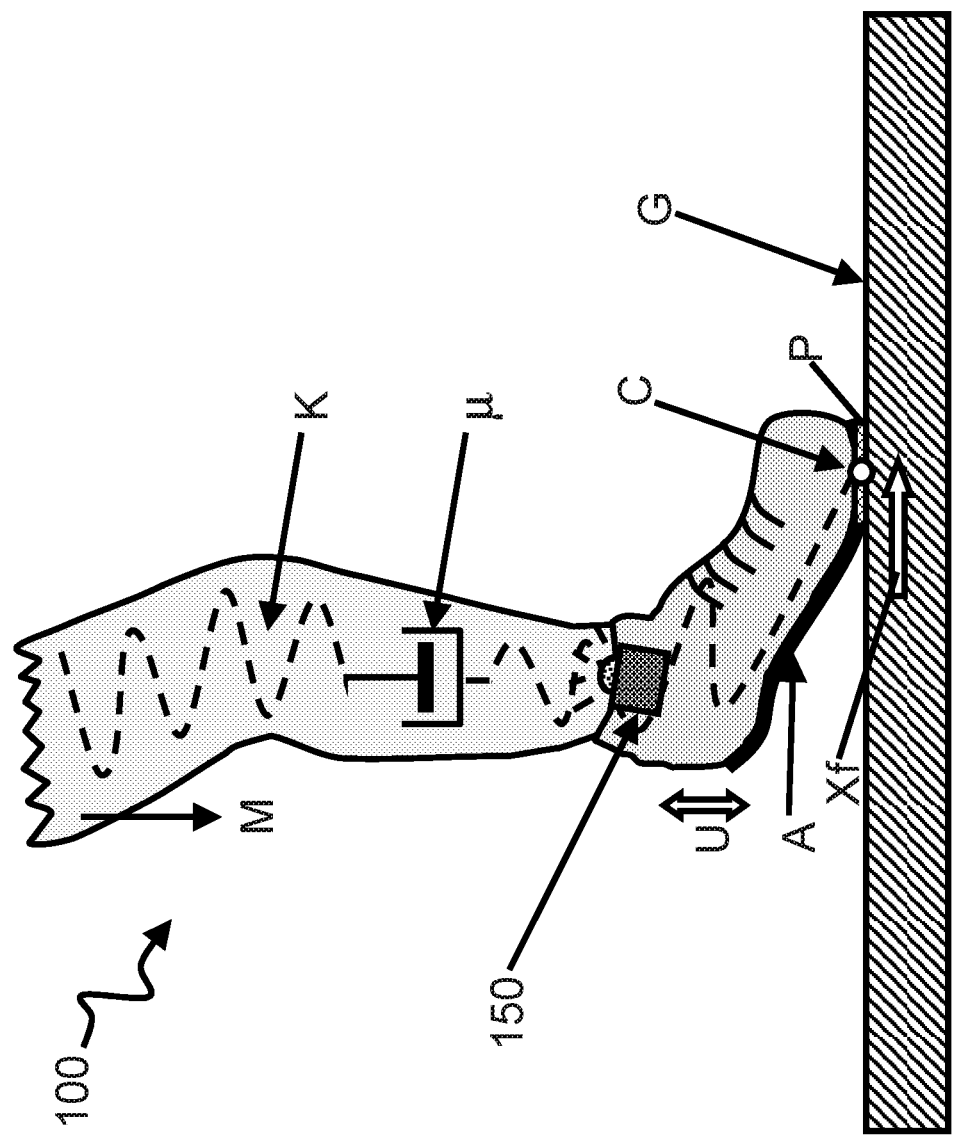
FIG. 1 schematically shows part of a running person that is wearing a shoe with an embodiment according to the second aspect.

The following description of certain exemplary embodiments is merely exemplary in nature and is in no way intended to limit the invention, its application, or uses. In the following detailed description of embodiments of the present systems, devices and methods, reference is made to the accompanying drawings which form a part hereof, and in which are shown by way of illustration specific embodiments in which the described devices and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. The following detailed description is therefore not to be taken in a limiting sense, and the scope of the present system is defined only by the appended claims. Moreover, for the purpose of clarity, detailed descriptions of well-known devices and methods are omitted so as not to obscure the description of the present system.

It is well documented that tendons can be very elastic and behave very much like a spring (Ker (1981) J. Exp. Biol. 93:283). A 10% increase in length can result in an elastic return of 93% of the work done in stretching a tendon. An example of this behavior can be made using the muscle-tendon unit of the lower leg during running. At the instance of first contact, the elastic elements of the muscle-tendon unit are stretched, storing energy before it is again released into the next step as the tendon elastically recoils. This type of action is often referred to as reactivity. This reactivity can mean that a portion of the energy exerted during vertical displacement can be recovered by storing and re-using it for the following step. The mechanics of the foot can also help this process of reusing energy in this example. During initial landing phase, the foot structure can deform storing more energy in the muscle tendon unit. See for example Ker, Bennett, Bibby, Kester & Alexander (1987), "The spring in the arch of the human foot" Nature 325:147-9. According to Tim Noakes book "Lore of Running" (1985) the combined elastic effects of the various components of the muscle tendon unit of the lower leg and foot, can reuse up to 50% of the energy required for vertical displacement. There are further elastic structures within the body which can contribute to this elastic behavior including the hamstrings and tractus iliotibialis. In this instance, when the pelvis rotates around the sagittal axis, the tractus iliotibialis can use the stored elastic energy for energy needed to raise the body's center of mass (Noakes, 1985).

The muscles and tendons below the knee and the structure of the foot, can be considered to work together as an efficient elastic spring. (Ker, Bennett, Bibby, Kester & Alexander, 1987. The spring in the arch of the human foot. Nature 325:147-9). A 70 kg man running at 4.5 m/s exerts a peak ground force of 2000 newtons. He loses and regains 100 joules (KE+PE) in each step.

|  | energy (J) | % return |
| --- | --- | --- |
| Achilles tendon | 35 | 93 |
| Arch of foot | 17 | 78 |
| Running shoes | 6-8 | 54-66 |
| Harvard track | 7 | 90 |

To work optimally the muscles of the muscle tendon unit must be appropriately co-coordinated to be reactive and create the most efficient motion. This is a very demanding task requiring great proprioception and co-ordination from the body. An efficient running requires much training instruction according to Noakes (1985), who states that that even a good runner must continuously practice to maintain his technique.

The principle of reactive running lies in the fact that the muscle action must react to the ground. For this action to be optimal tension, from pre-contracted muscles, must already be present in the leg prior to contact. This allows the elastic muscle-tendon unit segments to be loaded more effectively during landing. Essentially the contraction of the muscles is responsible for the effective loading of the elastic segments. It is also important that the contact time is short enough that the energy stored in the elastic elements of the muscle tendon unit is not dissipated through other mechanisms. Of course the placement of the foot can influence how useful the return energy is for the motion. The foot should be placed as close as is possible directly beneath the hip. Additionally landing on the heel is not so conducive to reactive running since it limits the number of elastic elements that may be recruited during contact. Noakes (1985) additionally states that together, brief ground contact and sufficient vertical displacement will help to save energy optimally during both energy-consuming partial movements.

The inventors have found that the difference between the afore mentioned Pose method and BK method can be objectively quantified in terms of a measurable parameter which will be referred to as the "running reactivity" or simply "reactivity" which infers the viscoelastic behavior of the muscle-tendon unit. In particular this running reactivity is modeled as a parameter that is proportional to a spring constant of a spring and/or inversely proportional to a viscoelasticity of a dashpot (damper) that is the equivalent for the viscoelastic properties of the subject's muscles and tendons e.g. during a footstep period from the moment the foot hits the ground until it is lifted off again. In a way the runner's body and legs are thought to act like the equivalent of a mass-spring-damper system. The spring constant of the connective tissue and muscle is found to be almost constant for any one individual, given a stable environment and physical state, so that in particular the state of contraction of the muscles can be used by the running subject to affect the total spring constant for the lower leg. It is thus found that to achieve higher elastic behavior, the running subject should pretense the muscles in his leg prior to landing. The more energy from landing reused in the next step, the more "reactive" the running style can be said to be.

The inventors observed that during forefoot running and in particular during sprinting, the center of pressure exerted by a subject through his foot on a pressure sensitive surface is sometimes moving backwards immediately after impact before moving forward again up until the foot is lifted from the ground. They attributed this phenomenon to the result, at least in part, of a process wherein (part of the) kinetic energy is absorbed into the connective tissues of the lower leg and temporarily stored as potential energy before (partly) being returned as kinetic energy in a useful direction for running. This process of storing kinetic energy into potential energy and vice versa was found akin to the way that a spring can store the energy of a moving mass. In this comparison, the running reactivity "R" of a running person's step is thus modeled as proportional to the spring constant (or elastic constant) "k" of a spring and inversely proportional to a viscosity "µ" of a dashpot/damper.

The inventors surprisingly found that the reactivity of a runner can be deduced and quantified from a measurement of the time-dependent center of pressure exerted on a surface during a running activity, e.g. using a pressure sensitive insole in the runner's shoe. In particular the inventors found a correlation between the time it takes the center of pressure to stop moving backward during a step (after landing) coupled with the distance it moves and the reactivity of that step as used in the BK method. Without being bound by theory, corroboration for this discovery is provided by the following discussion and equations.

Hooke's law, which is used for modeling the elasticity of a spring, states that:

$$F = -k\,x, \quad (E1)$$

wherein "F" is a force exerted by a spring with a spring constant "k" brought out of equilibrium by a displacement "x". The minus sign "−" indicates that the force "F" is opposite to the displacement "x".

Newton's law, governing the acceleration of masses, states that:

$$F = m\,a, \quad (E2)$$

wherein "F" is the force needed to accelerate a mass "m" with an acceleration "a". Because acceleration "a" is the second derivative of place "x" over time "t" this can also be written as:

$$F = m(d^2x/d\,t^2), \quad (E3)$$

Combining equations (E1) and (E3) yields $$d^2x/d\,t^2 = -(k/m)x. \quad (E4)$$

Solutions to this differential equation in terms of a time dependent displacement "x(t)" take the form of (a linear combination of) harmonic functions (e.g. sine and cosine functions) which oscillate with a natural frequency "Fn" of $$Fn = 1/(2Pi)SQRT[k/m] \quad (E5)$$

wherein Pi is the ratio between the circumference and diameter of a circle (valued approximately 3.14) and SQRT[ . . . ] is the square-root function, in this case of the spring constant "k" divided by the mass "m". By replacing the natural frequency "Fn" by the inverse of the time period "Tn" that it takes the spring to go through one full motion, the following equation is obtained:

$$1/Tn = 1/(2Pi)SQRT[k/m]; \quad (E6)$$

Squaring both sides yields:

$$1/Tn^2 = 1/(2Pi)^2(k/m), \quad (E7)$$

which can be written in terms of the spring constant "k" as:

$$k = (2Pi)^2(m/Tn^2). \quad (E8)$$

In this case "Tn" is the time period of the (periodic, back and forth) motion of a spring. The time period dT that it takes from the first moment that the foot strikes the ground T1 until the turning point T2 of the center of pressure (gait) line can be thought of as a quarter (one-fourth) of a natural spring motion period. This time period "dT" will be referred to as the "loading time", in analogy with the loading of a spring by a mass pressing on the spring. The relation between the natural spring period and the loading time is:

$$Tn=4dT. \tag{E9}$$

It is to be understood that other relations may exist between the natural frequency "Tn" and the loading time "dT", e.g. if the oscillation is an asymmetric or otherwise imperfect sine function and/or in case of a damped oscillation. Combining equations E8 and E9 yields:

$$k=(2Pi)^2(m(4dT)^2)=(Pi^2/4)m/dT^2. \tag{E10}$$

The spring constant k is a measure of how stiff the spring is. Since it is assumed that the muscle tendon unit behaves viscoelastically, the stiffer the "spring" the more elastic the system can be assumed to be (since a stiffer spring will be loaded at a faster rate given the same initial momentum). The more elastic the system, the more energy is reused and the more reactive the running technique can be considered to be, thus the reactivity "R" is a parameter that is proportional to the spring constant "k", i.e.

$$R \sim k, \tag{E11}$$

wherein the "~" sign signifies a proportionality relation. Combining E10 and E11 then finally yields:

$$R \sim 1/dT^2 \tag{E12}$$

Thus it is shown in a non-limiting example, that in cases wherein the center of pressure movement is indicative of at least part of a spring motion experienced by a running subject and relayed by the foot, the characteristic time period "dT" can be used to determine a spring constant "k" of the human "spring system" and thereby provide an objective measure for the reactivity of the running step. Thus in general terms it is shown that a measure for reactivity, also referred to as the "reactivity function" can be calculated as a function of the loading time "dT". It is further shown that a long loading time corresponds to a low reactivity and a short loading time corresponds to a high reactivity.

More in particular the reactivity "R" can be quantified (at least in terms of proportionality) by calculating the inverse of the square of a characteristic time period "dT", referred to as the loading time (of the spring). It is found that for determining the reactivity, this time parameter can be taken as the time of displacement of the center of pressure. In particular, this time parameter is found to be proportional to the time between the moment T1 that the foot first hits the ground and the moment T2 that the center of pressure reaches its most backwards position (e.g. with respect to a forward moving direction or a direction along the length of the foot). In other words, the time parameter is the time that it takes for a backward moving center of pressure to reach the turning point (where it starts moving forward again):

$$dT=T2-T1 \tag{E13}$$

It is noted that in case the first foot strike already provides the most backward position for the center of pressure (e.g. a heel strike), the time period would be zero and the reactivity as defined above infinite. However, on the contrary it is recognized that a runner landing on his heel typically has a minimal reactivity. Therefore, in an advantageous embodiment, the reactivity is defined zero or "undetermined" for a heel strike wherein the center of pressure does not move backwards during the footstep period, and/or any time period "dT" is below a certain minimum time threshold. In a further advantageous embodiment the reactivity can also be scaled or normalized by the distance that the center of pressure moves backwards thus giving a reactivity of 0 if there is no distance backwards It is further noted that using equation E10 it is also possible to determine in absolute terms a spring constant "k" (e.g. in Newton per meter) of the human spring system by inserting the parameters for a person's mass "m" and a measured time parameter "dT". This spring constant "k" could be used to define in absolute terms the reactivity "R", e.g. to compare a running reactivity between different subjects. Alternatively or in conjunction also a force measurement may be used to determine the spring constant.

It is noted that the above relation E12 between reactivity and time may also be deduced on the basis of a dimensional argument. For example, from equation E1 it is noted that a spring constant "k" and thus the reactivity "R" may be written in units of force divided by a unit of position (i.e. Newton/meter). From equation E2, or general principles, it can be shown that a force may also be expressed in units of mass (i.e. kilogram) multiplied by acceleration, which itself has units of position divided by time-squared (i.e. meter/second$^2$). Combining these two equations it can thus be shown that reactivity "R" can have the units of mass divided by time-squared. Accordingly it may be advantageous to calculate an inverse of the loading time dT as a defined running reactivity R and providing feedback as a function of the calculated running reactivity R.

It is finally noted that while the inverse of the square of the loading time "dT" is used here to provide an absolute (or relative measure) of the "running reactivity R" as defined in terms of an equivalent spring constant, in principle any function "f(dT)" of the loading time "dT" could be used to provide a user feedback on his running efficiency. In particular, a reactivity function could be defined as any function that correlates a shorter loading time "dT" with a higher reactivity "R" (i.e. defined more loosely as running efficiency) and a longer loading time "dT" with a lower reactivity "R".

As an example the reactivity "R" could be defined as any function that is inversely proportional to a power "P" of the loading time "dT", such as:

$$R \sim 1/dT^P \tag{E14}$$

wherein the exponent "P" is a positive real number (>0). It is noted that equation E12 is a particularly advantageous embodiment of equation E14.

In the following a more general model is presented wherein we consider a spring-mass-damper system. It will be shown that for such a system the exponent "P" of Equation 14 may be 1.

Depending on the requirements of the application this can take the form of a Maxwell model where the spring and damper are arranged in series. Alternatively the Kelvin model can be used as a simulation of muscle and tendons wherein the spring and damper are arranged in parallel. This can be extended into a more complex but more representative standard linear solid model or Zener model by adding an additional spring in series with the Kelvin model or in series with the damper.

In either case the damper or dashpot viscosity is the varying factor that is comparable to contracted muscle tension, more tension correlating with higher viscosity. The consequence of variations in either model will be a change in the time constant (t) of the system.

In any case using a viscosity model means that both time and displacement are important input parameters. In the case of the Maxwell model this is evident in the following calculation of total displacement from the force in the spring, the spring constant and dashpot viscosity:

Dashpot displacement:

$$dS^{total}/dt = dS^{dashp}/dt + dS^{spring}/dt$$

Where
$S^{total}$=total displacement
$S^{spring}$=displacement of spring
$S^{dashp}$=displacement of dashpot
t=time $$ds^{dashp}/dt = F^{dashp}/\mu$$

where:
$F^{dashp}$=force in dashpot
$\mu$=viscosity of dashpot $$dS^{spring}/dt = d(F^{spring}/k)/dt$$

where:
$F^{spring}$=force in spring
k=spring constant/elastic modulus
Thus:

$$dS^{total}/dt = F^{dashp}/\mu + d(F^{spring}/k)/dt$$

During normal running it can be assumed that the body weight of the runner remains relatively constant for the duration of the run. The acceleration of the falling foot can also be assumed to be relatively constant for most normal running styles since running involves a flight phase and acceleration due to gravity is constant, thus the total forces during impact should also be relatively constant. The rate of change of force may change on different surfaces or with different running techniques.

When the running surface is constant it can be assumed that changes in the rate of change of length of the "spring" (the muscle-tendon unit) are attributed to changes in the running technique. In the equation a larger value of $dS^{total}/dt$ thus results from more displacement or shorter loading time. It is assumed that the material properties of the muscle tendon unit do not change considerably during a run in a stable relatively constant environment thus the spring constant in the model also does not change, this means that changes in magnitude of displacement or time of loading can be assumed to be primarily influenced by the change in viscosity of the dashpot. The viscosity of the muscle tendon unit is modeled to be influenced by the muscle tissue contraction, with stronger contraction inferring a higher viscosity.

A higher viscosity results in more displacement distributed through the spring for the same force. This in turn results in more stored energy in the spring and subsequently more energy returned when the force is removed, thus resulting in a more reactive running style.

The model can be considered in terms of a graph of displacement versus time, or of strain (strain=dL/L, thus also related to displacement) versus time. Either way the time constant ($\tau$) can be visualized and calculated. In viscoelastic mechanics $\tau$ is defined as:

$$\tau = \mu/k$$

where
$\tau$=time constant
$\mu$=viscosity
k=elastic modulus

In this case k is assumed to be constant, thus $\tau$ is proportional to the viscosity $\mu$, which in this case corresponds to contraction strength of the muscle tissue. $\tau$ is used to calculate stress relaxation in a Maxwell model:

Stress relaxation=$ke^{(-1/\tau) \cdot t}$ $\tau$ is also used perhaps more appropriately for this application to calculate Kelvin model creep (strain versus time):

Creep function=$1/k(1-e^{(-1/\tau) \cdot t})$

The model that is used can be interchanged depending on the requirements of the application. In an advantageous embodiment the following method is used:
1. Measure vertical pressure with spatial resolution in time
2. Resolve the center of pressure (COP) from this measured data in time
3. COP is found to be related to heel position during normal running and walking gaits and this information can be used to estimate muscle tendon unit length.
4. The initial position of the COP can be identified at foot strike.
5. The movement of this centre of pressure back towards the heel is used as an input for a model (examples of this model are given e.g. Kelvin viscoelastic model)
   (b. During running gaits the time of flight between steps can also be used as an input to estimate the height of the body (assuming gravity is constant and take off and landing height are comparable) and coupled with the time of deceleration at impact, estimate the total force that will be exerted at the foot. This may be used to normalize the model inputs or to estimate absolute values of force and/or pressure, and any variables dependant on these parameters.)
6. The distance of the movement backwards of COP and the time are parameters used to estimate the time constant, T, of the system or time of loading of the spring in the system.
7. The more elastic the muscle-tendon unit behaves the stronger the muscle contraction (in the case of the viscoelastic models this is related to the viscosity of the dashpot), the more energy can be recovered and the more reactive the running style is said to be.

More elastic behavior means more energy is recovered from each step, and the more the connective tissue of the lower extremity is loaded and the higher the impact experienced by the runner and their joints and bones. These have implications for efficiency and for risk of injury that may be used to guide a user's technique depending on their personal needs and goals. A higher reactivity R is thus achieved for higher k and/or lower $\mu$, i.e. a system portraying elastic rather than viscous behavior. This thus means that a higher reactivity is achieved when the time constant, $\tau$, is lower. In a practical system, e.g. a measured loading time "dT" may be assumed to be proportional to the time constant $\tau$.

It may be said that reactivity changes depending on the contraction strength of muscle, or that reactivity is essentially a measure of the elasticity of the muscle-tendon unit, or the plyometric effect, or perhaps more generically the elasticity of the gait or running technique.

In an advantageous embodiment, a time-dependent center of pressure movement is related to a corresponding movement of the heel. This corresponding heel movement as a function of time is compared (i.e. fitted) to a viscoelastic model, e.g. Maxwell, Kelvin or Zener. From this comparison or fit, parameters may be extracted that relate to the viscous or the elastic parameters of the measured system (i.e. the running user). The user may then be provided with a measure of the reactivity of his running style e.g. by providing a reactivity parameter that is higher for higher elastic parameters k relative to the viscous parameters μ. For example, the reactivity may be inversely proportional to the aforementioned time constant τ.

With respect to the physiology, it is found that when muscles and tendons are stretched, their natural elasticity causes them to elongate and store potential energy, much like a spring. This potential energy may be released as these structures return to their normal length generating mechanical force. It is generally accepted that it is possible to influence running efficiency by utilizing the elastic structures of the muscles and tendons. Since the tendons cannot be actively controlled, the tension in the muscle is the predominant factor influencing the speed at which the unit stretches. To maximize the effect of elastic response during running, it is advantageous that the runner pre-tenses the muscle tissue prior to use thus making the muscles and tendons tight and able to absorb/store more elastic energy. Pre-tensing of muscles for the benefit of reactive running is advocated by various coaches, researchers and elite athletes in running technique to improve walking efficiency.

Further information may be found e.g. in:

"*Hip abductor weakness in distance runners with iliotibial band syndrome*" by Fredericson et al. (2000), Clin. J. Sport Med. July; 10(3):169-75 Department of Functional Restoration, Stanford University, California 943055105, USA;

"*Explosive Running: Using the Science of Kinesiology to Improve your Performance*" by Michael Yessis, Ph.D, (2000), Contemporary Books, Chicago, Ill.;

"*The mechanics of sprint running*" by Cavagna et al., J. Physiol. 1971 September 217(3): 709-721).

In general, the term "gait" refers to the pattern of movement of the limbs of a subject during locomotion over a solid substrate. Running is a means of terrestrial locomotion allowing a human or an animal to move rapidly on foot. Running is defined in athletics terms as a gait in which at regular points during the running cycle both feet are off the ground. A characteristic feature of a running body from the viewpoint of spring-mass-dashpot mechanics is that changes in kinetic and potential energy within a stride occur simultaneously, with energy storage accomplished by springy tendons and passive muscle elasticity. Time of flight or time off the ground indicates height of centre of mass, and landing force. The term running can refer to any of a variety of speeds ranging from jogging to sprinting. A footstep period may be defined as a period between a first moment after the foot starts touching the ground and a last moment before the foot is lifted from the ground.

It is found that when a running style involves a fore or mid-foot strike it is possible to use the muscles attached to the Achilles tendon to influence the behavior of the foot. A heel landing, aside from the inherent passive material properties of the structures of the foot, ankle and lower leg, does not allow this muscle-tendon unit to have so much effect on the storing or reusing of energy.

During a fore or mid foot landing the tension in the muscles associated with the Achilles tendon can be increased by contracting them making the muscle-tendon unit stiffer. The stiffer unit is consequently loaded faster by the applied impact forces and, due to its viscoelastic nature, behaves more elastically thus returning more energy i.e. more kinetic energy from impact is stored as potential energy in the muscle-tendon unit and used as kinetic energy in the subsequent motion.

The inventors found that, while running, the stretching of the muscle tendon unit could be observed in the foot pressure pattern of the runner. The centre of pressure can be observed moving a distance back towards the heel before moving forwards again towards the toe in the direction of movement. This "backward movement" of the centre of pressure is a consequence of the heel dropping towards the ground after the initial impact, essentially the two-dimensional centre of pressure position can be assumed to be correlated to heel position (lifted position i.e. distance from toe in length and height).

The height of the heel lift is assumed to correlate with the length of the muscle-tendon unit; in particular the change in heel lift may correlate with the change in muscle tension unit length. The absolute length of the tendon can be different for different people. The length of the muscle-tendon unit can be changed by relaxing the muscle or by elastically stretching either (or both) component(s) of the unit. Since it is the elasticity of the unit that is of interest in this instance, the state of contraction or relaxation of the muscle is not directly relevant. These aspects, however, may not easily be separated without the use of electromyography (EMG) equipment to measure the muscle activation state.

A completely relaxed muscle would provide almost no resistance to the impact at foot strike, resulting in no practically effective elastic stretching, and, likewise, a lengthening of a muscle tendon unit that is completely contracted can only be due to elastic stretching. Essentially the extent of possible elastic stretching can be assumed to be dependant on the level of muscular contraction.

Considering these factors, it is found that, based on the assumptions stated, the extent of elastic behavior of the muscle-tendon unit is dependant on the level of contraction and the speed at which it stretches. This effect is correlated to the extent and speed with which the heel drops after the initial foot strike, which can be estimated by measuring the speed and distance that the centre of pressure moves back away from the toes. The faster the center of pressure stops moving backward after landing, the more energy is reused, and thus by definition the more reactive the running technique. The amount of energy reused from a previous step for propulsion in the following step is essentially a function of the spring constant of the lower leg and/or the viscosity of the dampening (dashpot).

Further advantages and applications may become more apparent from the following detailed description of the drawings. This description again is to be regarded in an illustrative and non-limiting manner. In particular, steps and/or parts of the shown embodiments may be omitted and/or added without departing from the scope of the current methods and systems, which scope is defined by the appended claims.

FIG. 1 schematically shows part of a running subject 100, in particular the subject's leg and foot. The viscoelastic behavior of the muscles and tendons in the subject's leg and foot have been schematically represented by a spring with spring constant "K" and a damper with viscosity "μ". The spring and damper may be arranged in series (as shown in the figure), or alternatively in parallel or a combination thereof, depending on the appropriate viscoelastic model. While running, the subject's mass "M" exerts a pressure "P" through the leg and foot onto the ground "G". The resulting pressure profile can be measured e.g. by a pressure sensitive surface "A" placed between the foot and the ground. It is noted that where reference is made to the "ground", any walking or running surface may suffice.

During a footstep period, when a subject lands with his foot on the ground an increase in pressure is measured e.g. by an apparatus 150 and a first timestamp T1 is determined. When the subject lands on his forefoot as shown in FIG. 1, the center of pressure "C" will first be moving backwards as the subject "rolls" his foot over the ground and brings the back of his foot down over the shown axis "U" indicating a heel position. At a certain point in time, registered e.g. as a second timestamp T2, this backward moving pressure "C" will be reversed before the subject pushes off his foot and lifts it again from the ground repeating the process with his other foot (not shown here).

Figure 2:
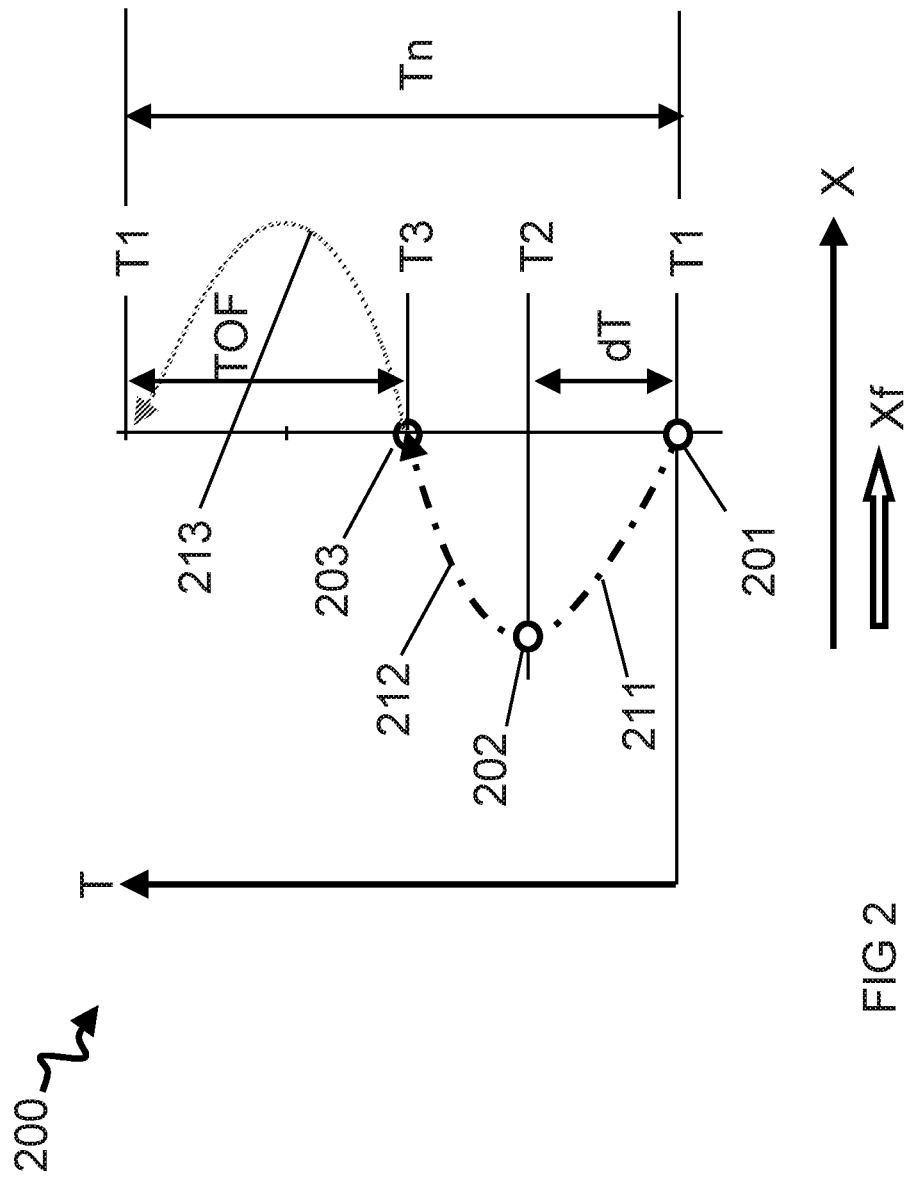
FIG. 2 schematically shows a recorded center of pressure line.

FIG. 2 schematically shows a graph 200 with a recorded center of pressure gait line of a foot on the ground during a running activity, measured along a coordinate X in a direction Xf as a function of time T. The first recorded center of pressure or landing point 201 at time T1 is followed by a backward moving center of pressure forming a gait line 211 until a reversal point 202 at time T2 is reached. The time period between T1 and T2 is referred to as the loading time "dT". The reversal point 202 is the most backwards registered position along the gait line (211, 212) with respect to the forward axis Xf. After the reversal, the center of pressure moves forward again forming the continued gait line 212 until a liftoff point 203 at time T3 is reached. In principle a reactive runner can be thought of as someone loading his human spring system (muscles and tendons) during the loading time dT and releasing the stored potential energy therein into his next step during the release time T2–T3.

The subsequent non-observed swing 213 of the spring is shown merely as an illustration to complete the imaginary oscillation of the human spring in a total period Tn. In particular this illustrates that the time difference dT=T2–T1 equals about one fourth the total natural oscillation period Tn of the human spring. In practice, only about half the oscillation (T1–T3) is observed and for the purposes of calculating the reactivity it may suffice to only record about a quarter oscillation T1–T2. It is noted that a heavily damped system may not oscillate.

Although the landing point 201 is shown in FIG. 2 at the same position as the liftoff point 203, these can and generally are at different locations, e.g. because the subject may start pushing off his foot at the end of the footstep period. Also the backswing or "loading" period T1–T2 may be different from the forward swing or "unloading" period T2–T3. The time of flight (TOF) may be the time between the liftoff point 203 and a next landing point 201.

The inventors have found that the reactivity is advantageously calculated from the period T1–T2, e.g. because this period is less influenced by anomalies caused e.g. by a subject keeping a longer contact with the ground when pushing off his foot around time T3. Such a pushing action is less indicative of the reactivity R of the step that is a desired parameter here. Furthermore, a backward going gait line is indicative of a forefoot landing which may provide a higher reactivity than a heel landing.

Figure 3:
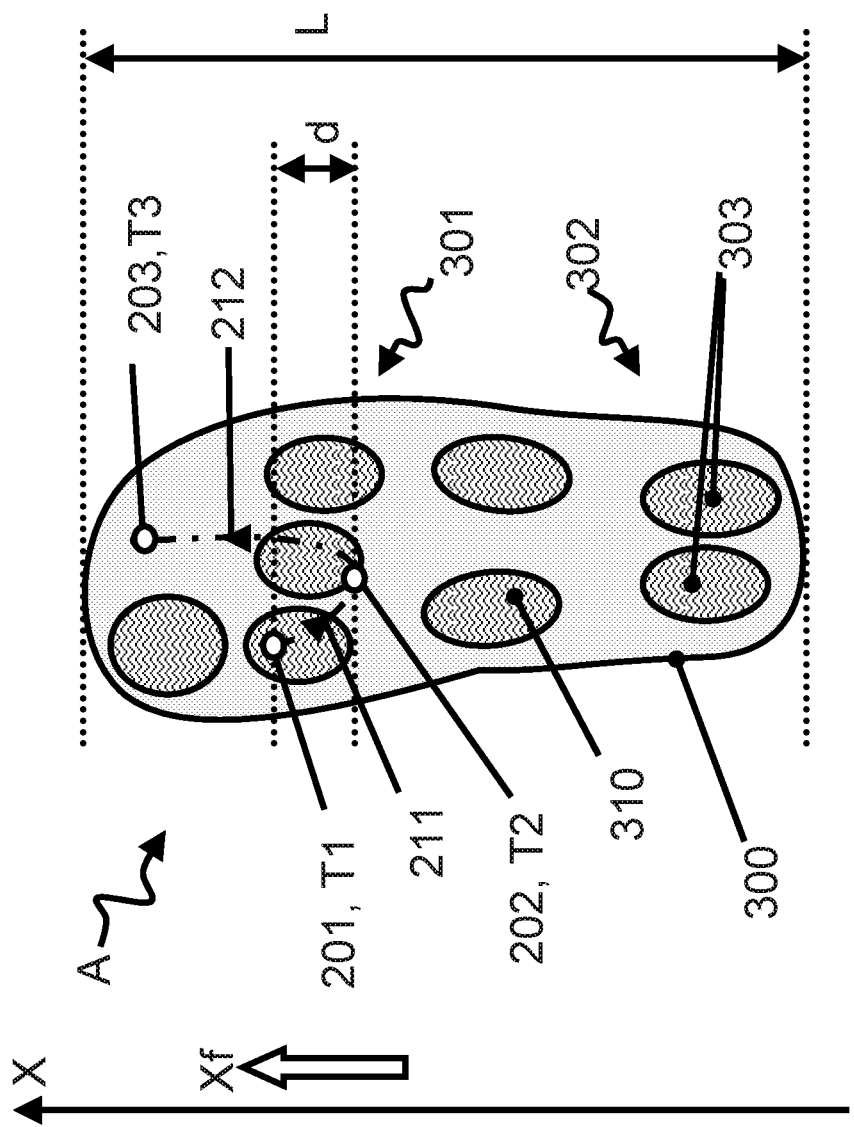
FIG. 3 schematically shows a pressure sensitive surface, suitable for wearing inside a shoe.

FIG. 3 schematically shows a pressure sensitive surface "A" comprising a plurality of pressure sensors 310. As shown the surface "A" can be suitably shaped as an insole 300 for wearing inside a shoe. The insole defines a front area 301 and back area 302 of the subject's foot. The pressure sensitive surface comprises front sensors at the front area and/or a heel sensor 303 at the back area. Shown on the surface "A" is an example gait line 211 comprising the backswing or loading part between the landing point 201 at time T1 and the reversal point 202 at time T2 and the subsequent forward swing 212 and liftoff point 203 at time T3. The center of pressure gait line 211, 212 is measured at least along a coordinate X in a forward running direction Xf, along the sagittal plane. In a practical embodiment the forward axis Xf can be equated with the length direction of the sole surface A, as shown. It is noted that even if this axis Xf would be rotated somewhat (e.g. up to 30 degrees), this would be of little consequence for measuring the timestamps T1 and T2 as defined above. The first impact moment T1 would still be the same while the reversal point 202 would change only negligibly (although slightly) thus having negligible influence on the timestamp T2.

Also shown is a loading distance "d" that is defined as the distance between the landing point 201 and the reversal point 202. This distance may be e.g. projected along the forward axis Xf, as shown, or alternatively may be measured or calculated as a line integral along the backswing gait line 201. Optionally, the loading distance "d" may be normalized by the foot length "L". The loading distance gives a measure of the distance that the foot (and leg) needs to reverse the backswing. It provides a measure e.g. of the shock that the subjects muscles and tendons have to endure during the spring action. A longer reactivity distance may correspond to a longer landing period. In that case, the longer this loading distance, the less shock is experienced by the subject. Such a measure of the loading distance may provide an additional piece of information to a runner about his running style, and his proneness/risk chance for injuries. E.g. a runner may wish to avoid too short a loading distance, or conversely he may want to shorten this distance e.g. by tensing his muscles and thereby possibly gaining reactivity.

A pressure sensitive surface "A" may comprise e.g. a plurality of pressure sensors that are suitably placed across the surface for measuring not only the amount of pressure exerted, but also the location where this pressure is measured. From a plurality of "n" measurements of pressure "Pn" at different locations "Xn" it is possible to calculate a location "Xc" of the center of pressure, e.g. through a calculation of the (normalized) first moment or weighted average position (weighted by pressure):

$$Xc = \mathrm{Sum}[Xn\, Pn]/\mathrm{Sum}[Pn], \tag{E15}$$

wherein Sum[ . . . ] is a summation over the "n" measurements.

It is noted that the positional variable "Xn" may be a scalar or vector representing a one or two-dimensional location, respectively, along the surface "A". The center of pressure location "Xc" may thus be calculated by weighting each pressure measurement by its magnitude and position so as to be able to resolve all forces into one point It is noted that for the purpose of calculating the running reactivity R it is only necessary to determine a first timestamp T1 when a foot starts touching the ground and a second timestamp T2 wherein a most backward pressure is measured by the pressure sensitive surface (relative to a forward axis Xf, also known as the "sagittal plane"). It is therefore only necessary to measure this pressure along the forward axis Xf, while it is also possible to map a two-dimensionally measured pressure onto this forward axis.

It is also noted that it not necessary to explicitly calculate the weighted average as given in E15. For example, it may also be possible to determine T1 and T2 by using two sensors at the front and back of the surface and, for setting T1, determining when a sudden increase in pressure is observed and, for setting T2, determining when the highest pressure is felt by the sensor on the back sensor scaled by the total pressure. In a further advantageous embodiment at least three pressure sensitive points that are not on a single line are used to determine a two dimensional center of pressure.

In an advantageous embodiment the heel sensor 303 can be used to determine a subject's heel is off the ground, e.g. if a heel pressure measured by the heel sensor 303 is below a threshold heel pressure. Correspondingly, in an advantageous embodiment a method is provided for determining a heel position wherein the steps comprise:

Defining a threshold pressure for a heel sensor at which the heel is said to be no longer in contact with the ground.

Resolving pressure sensors by magnitude and relative spatial position to define a centre of pressure Measuring the longitudinal distance of the center of pressure (COP) from the toe Defining a function for which the COP position is used to calculate the centre point of the heel position in which the radius of curvature of the heel path changes with the distance, (the closer the COP to the toe the larger the radius). This occurs as the axis of rotation moves across the ball of the foot with extension of the plantar fascia and the tarsal-metatarsal joints then around the joint of the metatarsal-phalanges joints then subsequently through the proximal/intermediate/distal phalange joints of the foot. It is assumed that the collective boney structures have a negligible flexibility and thus the radius of curvature predominantly correlates to the joints between these structures and that these joints articulate sequentially as is normally the case with healthy individuals. Knowing the size of the foot (or in this case it maybe sufficient to know the size of the insole or the distance between sensors since these are in the shoe or under the foot of the user so should correlate to the size of the foot to some degree) means it is possible to estimate the height of the heel from a scaling function based on the position of the COP and the associated radius of curvature.

An advantage of using a pressure sensor for determining the reactivity of a person is that pressure sensors are commonly available at reasonable prices, are light and thin, can easily be incorporated in for example a shoe or insole 300, and that the signal processing is straightforward. Advantageously, in addition to measuring the reactivity, the same pressure sensors can also be used to determine e.g. running parameters such as step rate, pronation rate and range, pressure distribution and other biomechanical parameters of a human In an advantageous embodiment the pressure sensitive surface may act as a weight measurement device for determining the weight or mass "M" of the user. In particular the subject's mass "M" may be calculated from a summation over a plurality of pressure measurements "Pn" and multiplying this sum by a calibration constant "Kc". If all pressure is measured by the pressure sensors that are exerted by the mass "M" on a surface "A", the mass may be calculated as:

$$M = \text{Sum}[Pn] \cdot A/g, \quad (E16)$$

wherein "g" is the gravitational constant valued approximately 9.8 m/s². The calibration constant "Kc" may thus be in this case be a conversion factor equal to the surface "A" divided by the gravitational constant "g". It is noted that if the pressure, measured by the surface, does not represent the full force of the user's weight, e.g. because not all pressure is recorded or he is standing on two legs while wearing only one insole, the calibration constant may be a linear or higher order function of the above mentioned A/g.

In an embodiment, the calibration constant may also be formed by a lookup table that correlates the measured pressure with a corresponding mass, which lookup table may be recorded at an earlier time. The mass may be measured in a mass measurement interval, e.g. the user may be prompted to stand still while his mass is measured at the beginning of a training exercise. Alternatively, the mass may be measured while the subject is running or walking, e.g. by averaging a measured pressure. In an embodiment wherein the user is wearing a pressure sensitive surface on only one foot, the pressure that is measured corresponds to about half the mass of the subject. Correspondingly, the calibration constant "Ke" may be doubled to retrieve the correct mass.

In a further advantageous embodiment, the feedback signal will not only be a function of the reactivity, but also of the mass of the user, e.g. as calculated by the device itself, or inputted separately by the user. In particular it is found, e.g. combining equations E10 and E11 or from general considerations that the reactivity is proportional to the user's mass "M" as well as inversely proportional to the square of the loading time "dT".

It is noted here that the force "F" of equations E1-E3 in principle may be similarly resolved from the total pressure "Sum[P]" when the area of application "A" is known since:

$$F = \text{Sum}[Pn] \cdot A. \quad (E17)$$

However, it is also noted that general insole pressure measurement systems currently available on the market may depend on the material properties of the insole to measure the pressure. Since insoles are generally made from soft elastic or viscoelastic materials they are vulnerable to dynamic effects such as hysteresis, relaxation time etc., that make it very difficult to resolve an absolute pressure measurement during the footstep period, restricting their use to relative measures of pressure. With this considered it may be difficult to simply estimate force from the measured relative pressure. Therefore the currently proposed measurement of the loading time "dT" provides an advantageous method of calculating the reactivity not easily achievable through other means.

Furthermore a force can be estimated from the loading time "dT" especially if the time of flight (TOF) is also known, e.g. the force can be estimated from the time of the movement of COP. The TOF is shown in the figure as the time between liftoff T3 and the time of landing T1 (of the next foot step). To measure the time of flight, preferably pressure sensors are provided for both feet.

The pressure of a foot at different locations can be measured by pressure sensors situated between the foot and the surface supporting the person such that the person's weight will actuate a pressure sensor. If in this document reference is made to the plural sensors it has to be understood that they need not to be physically separate devices. It may also be one sensor that allows measuring the pressure at different locations, for example a sheet of piezo-electric material with a matrix electrode.

Preferably the sensors are fixed in or on an insole that is placed in a shoe, such as shown in FIG. 3. This particular example of an insole 300 with pressure sensitive surface "A" comprises eight pressure sensors 310. Although it may be preferred that the sensors are fixed in or on an insole that is placed in a shoe, the sensors may for example also be attached to or placed in the shoe sole or glued to the foot sole. The sensors may even be mounted in or on the floor or any other convenient surface or interface between the foot and the surface on which the person is standing, walking, or running.

An advantage of a pressure sensitive insole compared to sensors on the floor is that the measurement is not bound to a specific location such as a specifically adapted floor, and that the number of sensors can be kept lower. In an alternative advantageous embodiment (not shown) the pressure sensitive surface can be part of the moving conveyor belt such as in running treadmill. An advantage of such an embodiment is that the runner can run long distances while not requiring an insole.

Examples of sensors that are suitable for measuring the pressure of the foot on the supporting surface are e.g. sensors based on electrical properties like capacitance (e.g. carbon laminate), inductance, or piezo-electric or piezo-resistance effects. However, also sensors based on optical properties, like reflectance or diffraction (e.g. Doppler shift, Bragg optical fibers) or color change (e.g. piezo-optic), may be suitable. An example of a pressure sensitive insole capable of measuring a gait line may be found also e.g. in U.S. Pat. No. 6,360,597. It is noted that any device capable of measuring a time dependent center of pressure exerted by a person's foot may be employed as a pressure sensitive surface.

Figure 4:
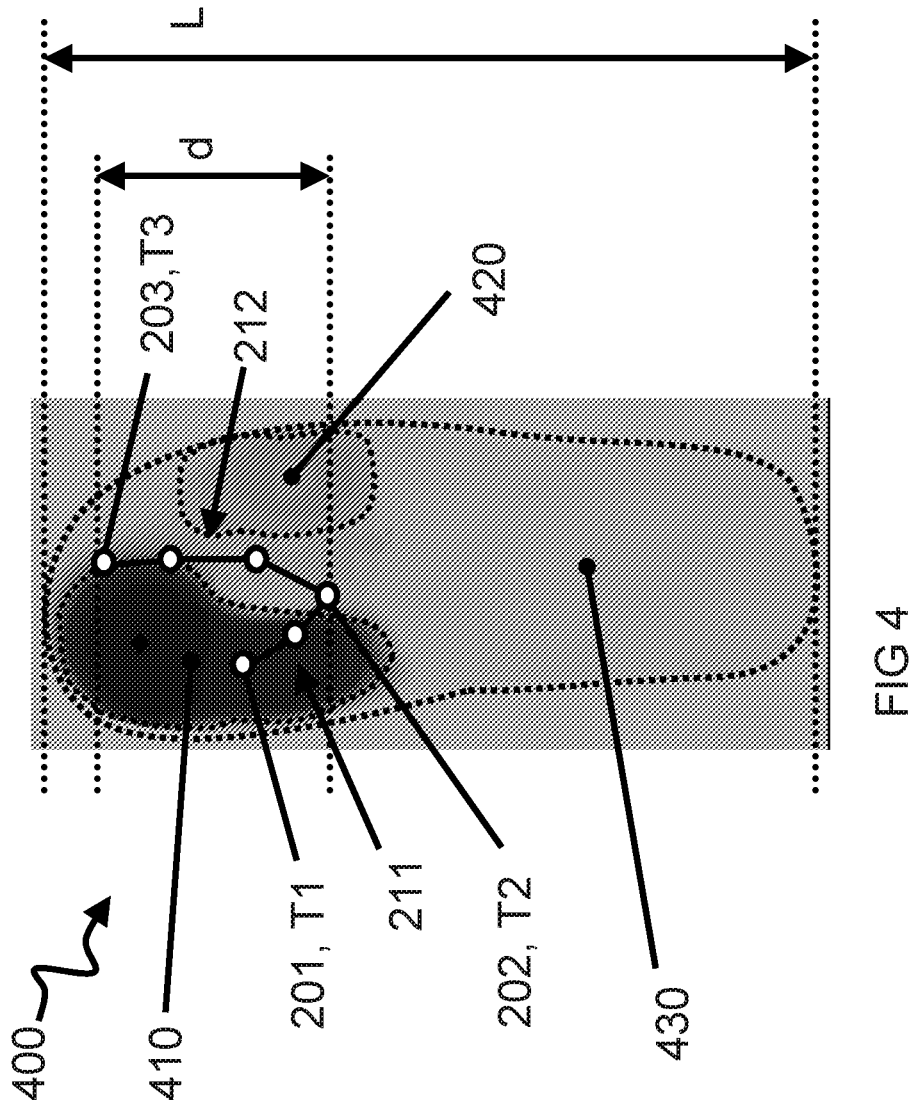
FIG. 4 shows a pressure map measured with a pressure sensitive surface such as shown in FIG. 3.

FIG. 4 shows an example of a pressure map 400 that was recorded using a pressure sensitive surface such as shown in FIG. 3. The pressure sensor used in this non-limiting example comprised a capacitive pressure sensing insole, as known in the art. The pressure map 400 shows a spatial pressure distribution that a foot exerts on a pressure sensitive surface at a specific moment in time. Areas of high pressure 410 are indicated with a lighter color and areas of low pressure 430 are indicated with a darker color. Areas of intermediate pressure 420 are also shown. This pressure map 400 that was measured e.g. at a time T can be processed e.g. using equation E15 to yield an average pressure point or centre of pressure position for that time T, in this case yielding the landing point 201 of the gait line 211, 212.

In the currently shown example of FIG. 4 a pressure sensor or array of pressure sensors was placed under the foot of a user. The output from the sensor(s) can be used to calculate the centre of pressure of the foot. Taking measurements one after another at regular time intervals allows the center of pressure position to be plotted in time forming a line which is commonly referred to as the "gait line". After landing, the location of the center of pressure at the first moment at which the total summed foot pressure passes a pre-defined contact threshold is defined as the "strike location". In the case that the center of pressure moves backwards in the sagittal plain towards the heel, the distance and time the center of pressure moves before changing direction and moving back towards the toe is measured. These values of time and center of pressure displacement are used as input into the reactivity or energy return model calculation.

Preferentially, the pressure at different locations of the foot is measured with a sampling frequency that is considerably higher than the frequency with which the foot strikes the ground during walking or running. In particular a sampling frequency of 50 Hz or higher may be advantageous. Such a high sampling frequency allows for a semi-continuous measurement of the centre of pressure position. The centre of pressure position at a given moment in time is the point where the resultant of all ground reaction forces acts at that moment.

As the pressure map changes during the step, so does the centre of pressure position. This time dependent average pressure point thus yields a line on the surface that is referred to as the "gait line". It will be understood that the gait line need not to be a line connecting points in space. The word gait line is used to describe the spatial distribution of the different centers of pressure during the contact time of the foot with the supporting surface.

Figure 5:
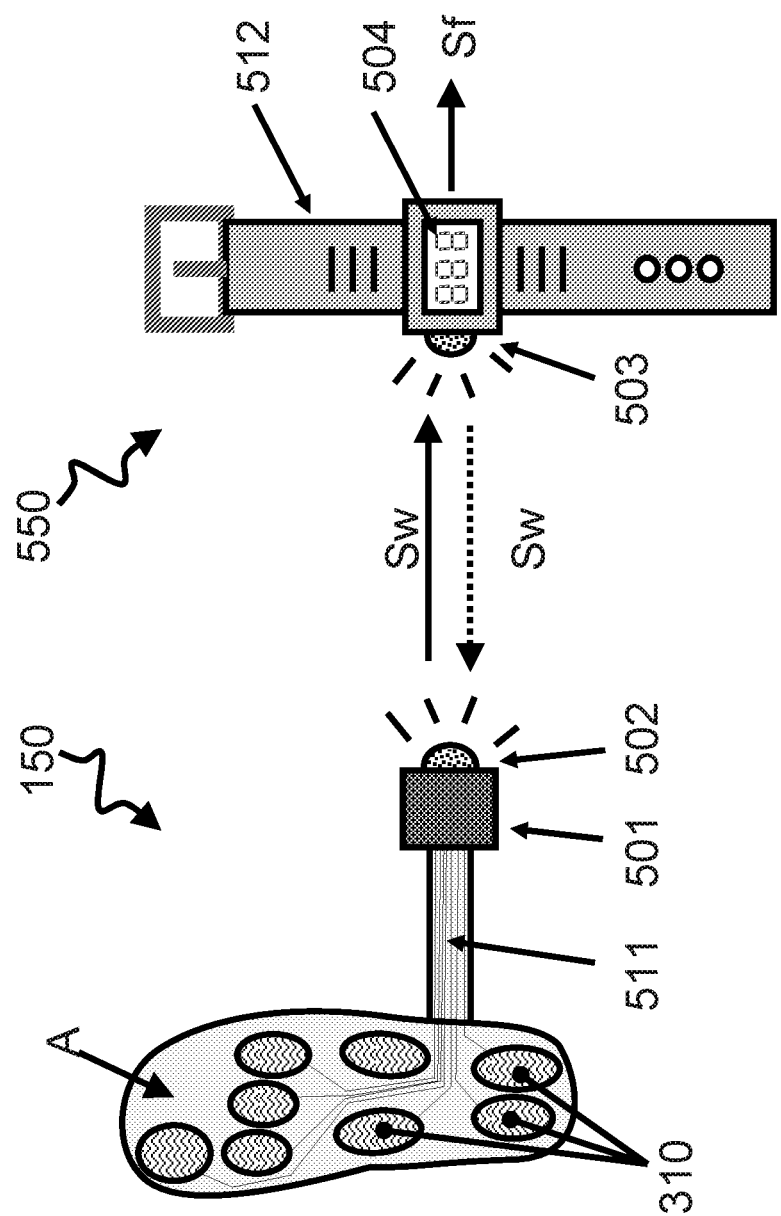
FIG. 5 schematically shows a two part embodiment of a system according to the second aspect wherein there is a wireless communication with a device according to the third aspect.

FIG. 5 schematically shows a two part embodiment of a system according to the first aspect wherein an apparatus 150 comprising a pressure sensitive surface "A" may wirelessly transmit data to a human interface device 550 according to the second aspect. In particular, during operation, an output electronic signal may be sent from a plurality of sensor pads 310 on the pressure sensitive surface "A", through electrical wiring 511 to a readout device 501. The readout device may comprise a processor to average the pressures yielding a center of pressure position or alternatively it may simply record all the different measured pressures and send the data onward, in which case the processor may be part of the human interface device 550. The data may be sent e.g. by a wireless transmitter 502 to a receiver 503. Both devices 502 and 503 may also comprise wireless transceivers that provide a two-way communication, e.g. for further control of the readout device 501 such as switching off the sensor for saving energy of a battery during times where there is no need for measuring the reactivity.

The human interface device 550 may have the form factor of a wrist watch with wrist strap 512 for convenient portability for the user. Alternative to a wrist band, the human interface device may e.g. comprise a Velcro or other attachment means interface that attaches e.g. to a patch of material on a user's upper arm, waist or anywhere else on his body. U.S. Pat. No. 4,578,769 shows an example of a combination of a foot sensor and a display device worn on the wrist that are capable of wireless communication.

The human interface device wearable on a subject's wrist, arm or other body part for providing a user with feedback on a running reactivity. The human interface device may comprise a wireless transceiver 503 for receiving a signal Sw indicative of the subject's running reactivity R, a display 504 arranged for displaying an image as a function of the received signal Sw of the subject's running reactivity and attachment means 512 for attaching the display 504 to a subject's wrist, arm, or other body part.

The human interface may thus comprise a display 504 providing a visual feedback signal "Sf" to the user as a function of the calculated reactivity R. The display may e.g. simply display a number that is proportional to the calculated reactivity and/or display a graph, e.g. a bar graph that extends as a function of the reactivity. The display could also provide a feedback by varying the color of a displayed image as a function of the calculated reactivity.

Besides visual feedback, the human interface device may also provide an audio feedback signal Sf, e.g. by modulating the pitch or volume of an acoustic feedback device as a function of the calculated reactivity. In particular the feedback device may comprise a loudspeaker and an audio controller arranged for producing an audio feedback signal via the loudspeaker according to, for example, a loudness, pitch, or pulse frequency of the audio signal as a function of the calculated running reactivity.

A further type of sensory feedback signal Sf may be provided e.g. by a haptic device that provides a haptic or tactile stimulus to the user, e.g. vibrating if the user runs above/below a preset reactivity threshold.

The output signal of the sensors can be sent to a communication or processing unit, for providing data for further analysis and processing in order to determine the reactivity of the step, either in real-time or later. The data may comprise for each sensor or for each location on a sensor the pressure and the time at which that pressure is measured. The communication unit may store the sensor data or send the data by wire or wirelessly to a processing unit suitable for automatic processing of the data. The processing unit and the communication unit may be incorporated within a single device or in separate devices.

A method according to which the person is carrying the processing unit may be advantageous for providing a person in real-time with information about his reactivity, for example optically, using a display or signal lamps, e.g. a row of LEDs forming a bar graph of the user's reactivity, or acoustically, using a recorded voice or a signal sound. Furthermore e.g. a mobile phone or "smart phone" or internet phone or computer screen or any other media could be used to display the information.

Figure 6:
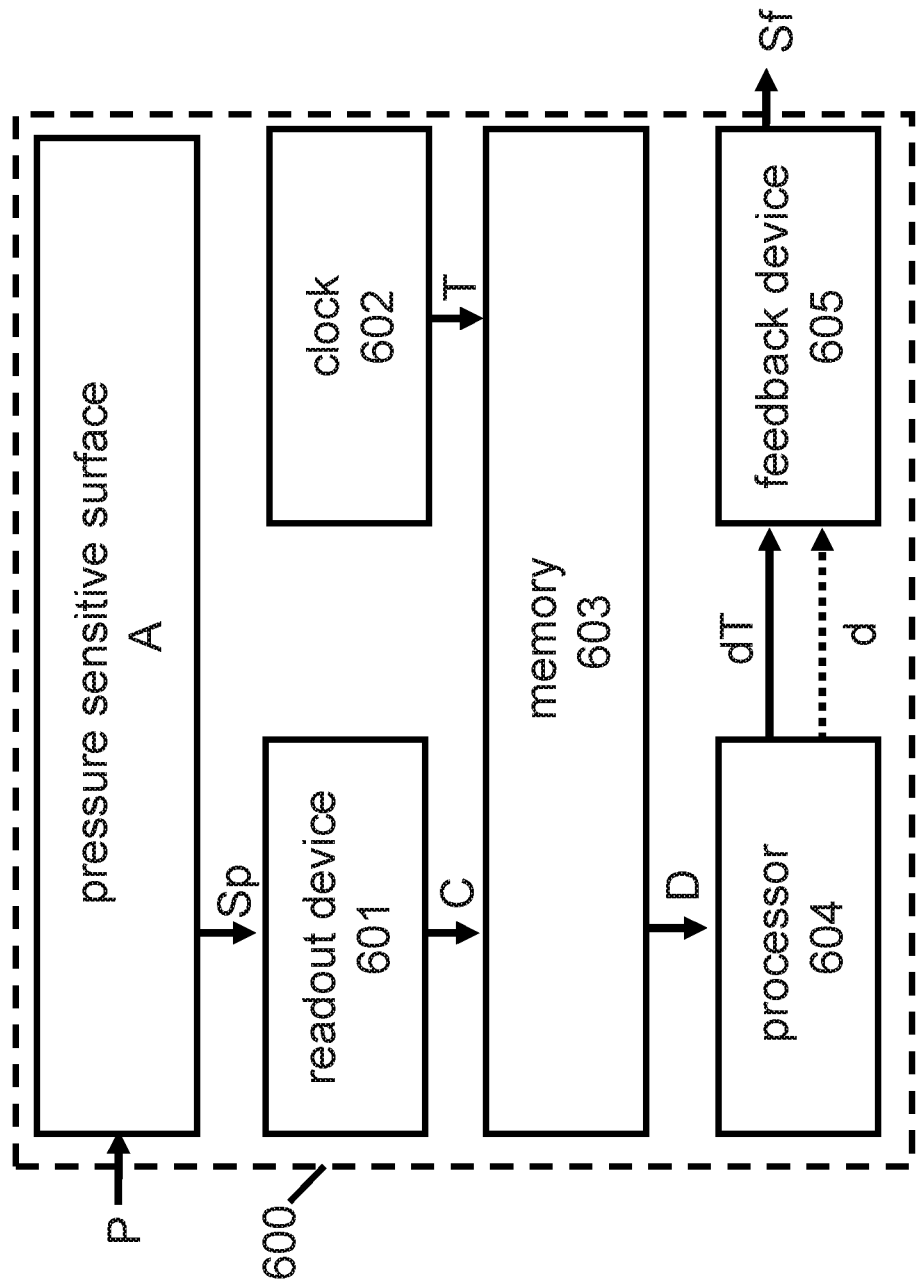
FIG. 6 schematically shows an embodiment of a system according to the second aspect.

FIG. 6 schematically shows an embodiment of a system 600 for providing feedback Sf on a subject's running style. During a running activity, a subject applies through his foot a pressure P on a pressure sensitive surface A. This pressure is recorded by a readout or measuring device 601 which may convert the overall pressure Sp to a center of pressure signal C that is stored in memory 603 in conjunction with a time stamp T provided by a clock 602. The thus recorded time dependent center of pressure C(T) forms the data D that can be read out by the processor 604 from the memory 603 together with other parameters, which can be provided to the memory separately. These other parameters e.g. comprise the weight of the running subject, height, shoe size, age, acceleration, location etc.

The processor 604 may determine from the data the timestamps T1 and T2 of the landing and turning point in the gait line C(T). In an embodiment, the processor first determines if the subject landed on his heel or forefoot, e.g. from a threshold on the location of the first measured center of pressure at the beginning of a foot landing. If the footstep is determined to be a heel strike a reactivity of zero is passed on to the feedback device. If a forefoot landing is determined, the calculation of the reactivity continues.

The landing time T1 may be assigned as the time that a sudden increase in pressure is observed, e.g. at the moment that a foot first starts touching the ground. The turning time T2 may be deduced from the trajectory of the gait line C(T) as the time that the line reaches the most backward position with respect to the forward axis. From a time difference dT between T1 and T2, the loading time dT may be calculated. A reactivity R may calculated as a function of the loading time dT and distance and be used to control the feedback device 605, e.g. a display, acoustic device, or haptic device. The feedback device may provide the user with a feedback signal Sf informing him of the reactivity of his step. This reactivity may be e.g. a step by step updated value or a moving average over any number of steps.

The memory 603 may be any suitable type of memory where data are stored, (e.g., RAM, ROM, removable memory, hard drives, floppy disks, memory cards, etc.) or may be a transmission medium or accessible through a network (e.g., a network comprising fiber-optics, the world-wide web, cables, or a wireless channel using time-division multiple access, code-division multiple access, or other radio-frequency channel). Any medium known or developed that can store and/or transmit information suitable for use with a computer system may be used as the computer-readable medium and/or memory. The memory may also store application data as well as other desired data accessible by the controller/processor 604 for configuring it to perform operational acts in accordance with the present systems and methods. Any type of processor may be used such as dedicated or shared one.

The processor 604 may include micro-processors, central processing units (CPUs), digital signal processors (DSPs), ASICs, or any other processor(s) or controller(s) such as digital optical devices, or analog electrical circuits that perform the same functions, and employ electronic techniques and architecture. The processor is typically under software control for example, and has or communicates with a memory that stores the software and other data such as user preferences, parameters, evaluation ranges, and/or time, bandwidth, and fraction thresholds.

The clock 602 may be any instrument capable of providing an indication of a passing of time. In particular the clock need not keep an absolute measure of time, since only a time difference "dT" is required for the determination of the reactivity. The clock need not necessarily conform to any standard timing device, in particular it is not necessary for the clock to provide time in standard units such as seconds, minutes or hours. Any unit used by the clock may suffice as long as it is a linear in time.

The pressure sensitive surface "A", readout device 601, clock 602, memory 603, processor 604, and feedback device 605 may all or partly be a portion of a single (fully or partially) integrated unit 600 such as any wearable or contactless device. Alternatively, instead of being integrated in a single device, parts may be distributed between multiple devices, e.g. a separate pressure sensitive surface and/or feedback device. Between any of the shown parts a wired or wireless interface may be present to transmit and receive signals between the devices or portions thereof. In addition, the apparatus or system 600 may comprise a battery for power supply or for example solar cells. In an embodiment the pressure sensors may even be powered by the footsteps of the user.

In the shown system 600 a further parameter value may be calculated for the loading distance "d", which may be defined as the distance between the center of pressure locations at T1 and T2. The distance may either be measured along a fixed axis, e.g. the forward axis or the distance may be calculated as a line integral along the gait line between the center of pressure locations at times T1 and T2. This calculated loading distance "d" may be used to provide the user of further feedback on his running style. The feedback device 605 may be controlled by the processor 604 to provide the feedback signal Sf as a function of both the loading time "dT" and the loading distance "d".

In a further advantageous embodiment, the loading distance "d" may be scaled as a proportion of the total foot size. In addition the foot size may also be used to normalize the measure of reactivity. The factor may additionally be normalized by the user's body weight and age. This may provide advantages for comparing reactivities between different runners. Furthermore the reactivity may be normalized as a function of a time of flight (TOF). The TOF may be defined as the time between a last registered moment that the subject's foot stops touching the ground (T3) and the first registered moment (T1) that the subject's foot starts touching the ground, i.e. the time that the subject is registered as not touching the ground.

In an advantageous embodiment the memory 603 comprises a conversion table for converting the moving center of pressure C to a moving heel position U (see FIG. 1). The processor is further arranged for converting the moving center of pressure C to a moving heel position U and controlling the feedback device 605 to generate the feedback signal Sf as a function of the moving heel position U.

In a further advantageous embodiment the memory comprises threshold values for a minimum or maximum desired heel acceleration. The processor calculates the heel acceleration from the moving heel position and compares this calculated heel acceleration to the threshold heel acceleration. The processor then controls the feedback device to generate a feedback signal as a function of this comparison, e.g. depending if the calculated heel acceleration falls inside or outside the threshold heel acceleration values.

In yet a further advantageous embodiment, the pressure sensitive surface comprises a heel sensor 303 (see FIG. 3) and the processor is arranged for converting the moving center of pressure C to a moving heel position U if a heel pressure measured by the heel sensor is below a threshold heel pressure. In particular it is noted that the center of pressure may be related to a heel position if the heel is off the ground.

Figure 7:
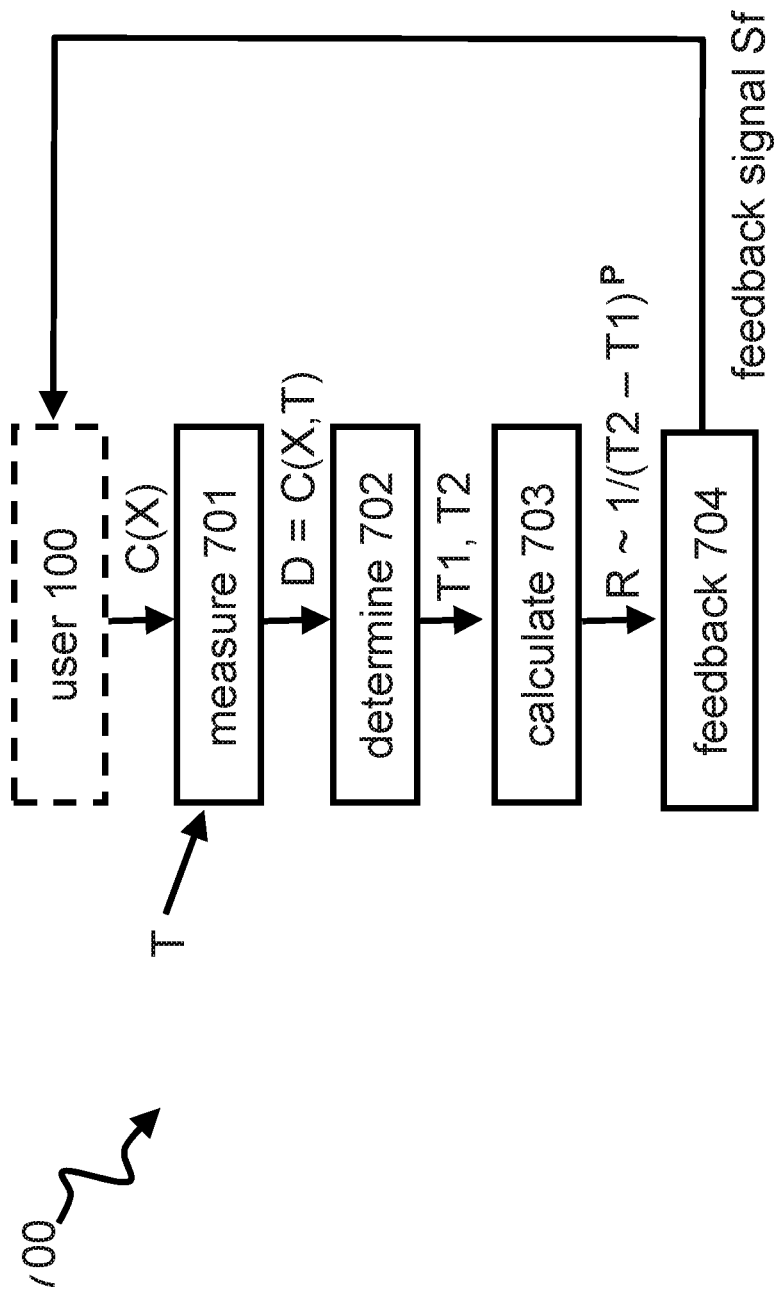
FIG. 7 schematically shows an embodiment of a method according to the first aspect.

FIG. 7 schematically shows an embodiment of a method 700 for providing a user feedback on his running reactivity R. In the method a center of pressure position C along a coordinate X is measured (step 701) and stored as data D as a function of time T. This data forms a gait line from which a first and second timestamp T1 and T2 are determined (step 702) corresponding to the landing time T1 and the turn-around time T2 that is the time corresponding to the most backwards measured center of pressure point C along the axis X. From the two timestamps T1 and T2 a reactivity is calculated (step 703), in this case defined proportional to the inverse of the square of the time difference dT=T2-T1. The reactivity is used to provide a user with a feedback signal Sf as a function of the reactivity R.

It is to be appreciated that any function of the loading time dT with or without the loading distance could in principle be used to provide a user feedback on his reactivity. In an extreme example, this time dT with or without the loading distance could simply be provided to the user without further processing, where the user himself may interpret that a reactivity is higher for lower loading times. It is to be appreciated that in general a feedback signal as a function of the loading time "dT" should provide the user with an indication of a lower reactivity "R" for higher loading time and of a higher reactivity for lower loading times, with the notable exception of a heel landing wherein the loading time may be defined as zero while the reactivity may also be negligible.

In an advantageous embodiment, the output or feedback signal Sf may be a value proportional to the amount of the energy returned to useful work via the elasticity of the system. The output value can be used as a relative measure to monitor proportional changes in the amount of reused energy/reactivity. The output can also be normalized using additional parameters such as weight, height, shoe size, and center of pressure displacement e.g. scaled by the ratio of center of pressure displacement: foot size and multiplied by weight (normalizing for size and weight). Alternatively the potential efficiency can be determined experimentally to define the value of the scaling factor required to convert the output of the model to mechanical efficiency or % of maximum possible reactivity/elasticity.

The various elements of the embodiments as discussed and shown offer certain advantages, such as providing an indication of the reactivity and/or running efficiency. Of course, it is to be appreciated that any one of the above embodiments or processes may be combined with one or more other embodiments or processes to provide even further improvements in finding and matching designs and advantages. It is appreciated that this invention offers particular advantages for defining the reactivity as the inverse of the square of the loading time dT and in general can be applied for producing any feedback signal "Sf" in the form of a reactivity/efficiency or other relevant running parameter, that is a function of the loading time and/or loading distance.

Finally, the above-discussion is intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the broader and intended spirit and scope of the present system as set forth in the claims that follow. The specification and drawings are accordingly to be regarded in an illustrative manner and are not intended to limit the scope of the appended claims.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise; no specific sequence of acts or steps is intended to be required unless specifically indicated; and no specific ordering of elements is intended to be required unless specifically indicated.

The invention claimed is:

1. A system for generating feedback on a subject's running style, the system comprising:
 a pressure sensitive surface with a plurality of pressure sensors for generating an electronic signal as a function of a pressure exerted on said pressure sensitive surface;
 a clock arranged for providing timestamp information;
 a memory arranged for storage and retrieval of data;
 a readout device arranged for reading out the plurality of pressure sensors and the clock and storing data in the memory comprising a time-dependent measurement of a moving center of pressure exerted by a subject's foot on the pressure sensitive surface, the moving center of pressure forming a pressure gait line at least distinguished along a forward axis of a running direction; and
 a feedback device arranged for generating one or more of a visual, audio, or haptic feedback signal and controlled by a processor, said processor arranged for:
 reading the data from the memory;
 determining from the data a first timestamp at a first registered moment that a front portion of the subject's foot starts touching the ground;
 determining from the data a second timestamp at a moment that the center of pressure reaches a most backwards registered position along the gait line with respect to the forward axis;
 calculating a time difference between the first and second timestamps as a defined loading time; and
 controlling the feedback device to generate a feedback signal as a function of the loading time.

2. The system according to claim 1, wherein the processor is further arranged for:
- calculating a distance between the measured center of pressure at the moment that the first timestamp was recorded and the measured center of pressure at the moment that the second timestamp was recorded as a defined loading distance (d); and
- controlling the feedback device to generate the feedback signal as a function of the calculated loading distance.

3. The system according to claim 1, wherein
- the memory comprises a conversion table for converting the moving center of pressure to a moving heel position; and
- the processor is further arranged for converting the moving center of pressure to a moving heel position and controlling the feedback device to generate the feedback signal as a function of the moving heel position.

4. The system according to claim 3, wherein the pressure sensitive surface comprises a heel sensor and the processor is arranged for converting the moving center of pressure to a moving heel position if a heel pressure measured by the heel sensor is below a threshold heel pressure.

5. The system according to claim 1, wherein the pressure sensitive surface is shaped as an insole for placement inside a shoe wherein the insole defines a front and back area of the subject's foot and the pressure sensitive surface comprises front sensors at the front area and/or a heel sensor at the back area.

6. The system according to claim 1, wherein the processor is further arranged for calculating an inverse of the loading time as a defined running reactivity and controlling the feedback device to generate a reactivity feedback signal as a function of the calculated running reactivity.

7. The system according to claim 1, wherein the processor is further arranged for:
- calculating during a mass measurement interval the subject's mass from a summation of a total measured pressure and multiplying this sum by a calibration constant; and
- controlling the feedback device to generate the feedback signal as a function of the subject's mass.

8. The system according to claim 1, wherein the processor is further arranged for:
- determining a time of flight between a last registered moment that the subject's foot stops touching the ground and a first registered moment that the subject's next foot starts touching the ground; and
- normalizing the feedback signal as a function of the time of flight.

9. The system according to claim 1, wherein the feedback device comprises a loudspeaker and an audio controller arranged for producing an audio feedback signal via the loudspeaker according to a loudness, pitch, or pulse frequency of the audio signal as a function of the calculated running reactivity.

10. A method for generating feedback on a subject's running style, the method comprising the steps of:
- receiving data comprising a time-dependent measurement of a moving center of pressure exerted by the subject's foot on a pressure sensitive surface, the moving center of pressure forming a pressure gait line at least distinguished along a forward axis of a running direction;
- determining from the data a first timestamp at a first registered moment that a front portion of the subject's foot starts touching the ground; determining from the data a second timestamp at a moment that the center of pressure reaches a most backwards registered position along the gait line with respect to the forward axis;
- calculating a time difference between the first and second timestamps as a defined loading time; and
- controlling the feedback device to generate a feedback signal as a function of the loading time.

11. The method according to claim 10, wherein the feedback signal is generated as a function of a calculated loading distance between locations of a measured center of pressure at the moment that the first timestamp was recorded and a location of the measured center of pressure at the moment that the second timestamp was recorded.

12. The method according to claim 10, further comprising the step of calculating an inverse of the loading time as a defined running reactivity and controlling the feedback device to generate a reactivity feedback signal as a function of the calculated reactivity.

13. The method according to claim 10, wherein the calculated running reactivity is multiplied by the subject's mass prior to generating the feedback signal.

14. The method according to claim 13 wherein the subject's mass is calculated by adding the total measured pressure exerted by the subject's foot on the pressure sensitive surface and multiplying this total measured pressure by a calibration constant.

15. A human interface device wearable on a subject's wrist or arm for providing a user with feedback on a running style, the device comprising:
- a wireless transceiver arranged for receiving a signal indicative of the subject's running reactivity, the running reactivity defined as a parameter inversely proportional to a measured time period between a first moment that a front portion of a foot of the subject hits the ground and a second moment that a center of pressure, exerted by the subject's foot reaches a most backward position with respect to the subject's running direction;
- a display arranged for displaying an image as a function of the received signal of the subject's running reactivity; and
- attachment means arranged for attaching the display to the subject's wrist or arm.

* * * * *

UNITED STATES PATENT AND TRADEMARK OFFICE
CERTIFICATE OF CORRECTION

PATENT NO. : 9,687,712 B2
APPLICATION NO. : 14/235920
DATED : June 27, 2017
INVENTOR(S) : Statham et al.

It is certified that error appears in the above-identified patent and that said Letters Patent is hereby corrected as shown below:

On the Title Page

Assignee now reads:
"Nederlandse Organisatic voor toegepast-naturrweten schappelijk onderzoek TNO"

Should read:
-- Nederlandse Organisatie voor toegepast-natuurwetenschappelijk onderzoek TNO --

Signed and Sealed this
Twelfth Day of September, 2017

Joseph Matal
*Performing the Functions and Duties of the
Under Secretary of Commerce for Intellectual Property and
Director of the United States Patent and Trademark Office*